United States Patent
Werner

[11] 3,939,267
[45] Feb. 17, 1976

[54] 4-ETHERS OF 3-AMINO-5-SULFAMOYLBENZOIC ACIDS
[75] Inventor: Lincoln Harvey Werner, Summit, N.J.
[73] Assignee: Ciba-Geigy Corporation, Ardsley, N.Y.
[22] Filed: Oct. 13, 1972
[21] Appl. No.: 297,530

[52] U.S. Cl. .................................. 424/319; 424/310
[51] Int. Cl.² ...................... A01N 9/20; A01N 9/24
[58] Field of Search ............................ 424/319, 310

[56] References Cited
UNITED STATES PATENTS
3,163,645 12/1964 De Stevens et al. ................. 424/229
3,806,534 4/1974 Feit ............................... 260/465 D Primary Examiner—Jerome D. Goldberg
Assistant Examiner—D. W. Robinson
Attorney, Agent, or Firm—Joseph G. Kolodny; Theodore O. Groeger; John J. Maitner

[57] ABSTRACT

4-Phenylethers of 3-amino-5-sulfamoylbenzoic acids, e.g. those of the formula

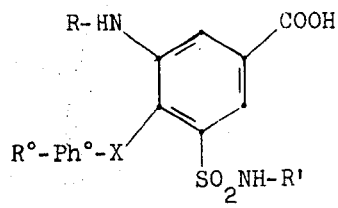

R = an aliphatic or araliphatic radical
X = O or S
Ph° = a phenylene radical
R' = H, alkyl or Ph°—R''
One of R° and R'' is NH₂ and the other is H
alkyl esters or salts thereof are diuretic agents.

4 Claims, No Drawings

4-ETHERS OF 3-AMINO-5-SULFAMOYLBENZOIC ACIDS

BACKGROUND OF THE INVENTION

Pursuant to the discovery of the diuretic 4-halo-5-sulfamoyl-anthranilic acids, substituted at the sulfamoyl moiety by an araliphatic or aromatic radical, described in my U.S. Pat. Nos. 3,565,920 or 3,658,990, there was generated a new class of primary amino compounds herein described, which members surprisingly do not require a halogen atom or a tertiary amino group at the aromatic nucleus, thought to be essential for diuretics, such as the chlorothiazides, hydrochlorothiazides or said anthranilic acids, or the sulfamoylbenzoic acids described in U.S. Pat. Nos. 2,937,169 and 3,163,645 or Belgian Patent No. 743,744 respectively.

SUMMARY OF THE INVENTION

The present invention concerns and has for its object the provision of new 4-phenylethers of 3-amino-5-sulfamoylbenzoic acids and the lower alkyl esters and therapeutically acceptable salts thereof, more particularly of those corresponding to Formula I

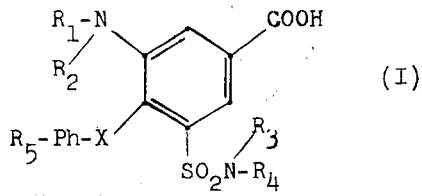

in which $R_1$ is an aliphatic or araliphatic radical, each of $R_2$ and $R_3$ is hydrogen or lower alkyl, X is oxygen or sulfur, Ph is a phenylene radical, $R_4$ is hydrogen, lower alkyl or $R_6$—Ph and one of $R_5$ and $R_6$ is amino and the other hydrogen, the lower alkyl esters or therapeutically useful ammonium, alkali or alkaline earth metal or acid addition salts thereof, as well as of corresponding pharmaceutical compositions and of methods for the preparation and application of these products, which are useful, orally applicable diuretic, natri- and chloriuretic agents.

DESCRIPTION OF THE PREFERRED EMBODIMENTS

An aliphatic radical $R_1$ is, for example, lower alkyl, e.g. methyl, ethyl, n- or i-propyl, n-, i- or sec. butyl, n- or i-pentyl, neopentyl, n-hexyl or n-heptyl; lower alkenyl, e.g. vinyl, allyl, methallyl or 2-butenyl; lower alkynyl, e.g. propargyl; mono- or bicyclic cycloalkyl, cycloalkenyl, cycloalkyl-lower alkyl or cycloalkenyl-lower alkyl with preferably 3 to 7 ring-carbon atoms, 1to 4 chain carbon atoms and optional, e.g. up to 4, lower alkyl groups, e.g. cyclopropyl, 2,3-dimethylcyclopropyl, cyclobutyl, cyclopentyl, 2- or 3-methylcyclopentyl, 2,5- or 3,4-dimethyl-cyclopentyl, cyclohexyl, 2-, 3- or 4-methylcyclohexyl, 2,3- 2,4- or 3,5-dimethyl-cyclohexyl, 2,4,6-trimethylcyclohexyl, cycloheptyl, cyclooctyl, 2- or 7-norbornanyl, 1- or 2-decahydronaphthyl; 1- or 2-cyclopentenyl, 2,4-cyclopentadienyl, 2- or 3-methyl-2-cyclopentenyl, 4,5-dimethyl-2-cyclopentenyl, 1-, 2- or 3-cyclohexenyl, 2,5-cyclohexadienyl, 2-, 3- or 4-methyl-1- or 2-cyclohexenyl, 2,4- or 3,5-dimethyl-1- or 2-cyclohexenyl, 2,4,6-trimethyl-2,5-cyclohexadienyl, 1-, 2- or 3-cycloheptenyl, 2,6-cycloheptadienyl, 2-cyclooctenyl or 2-norborn-5-enyl, as well as the corresponding cycloalkyl- or cycloalkenyl-lower alkyl groups in which the chain especially represents methyl, but also ethyl n- or i-propyl, n-, i- or sec. butyl; it contains in any of the positions available for substitution one of the specific cycloalkyl or cycloalkenyl groups listed above. The term "lower", referred to above and hereinafter in connection with organic radicals or compounds respectively, defines such with up to 7, preferably up to 4, carbon atoms.

Said aliphatic radicals, especially the lower alkyl groups, can be substituted, e.g. by free or functionally converted hydroxy, mercapto or carboxy groups and/or interrupted by heteroatoms, e.g. one oxygen, sulfur and/or nitrogen atom, and are represented, for example, by lower haloalkyl, e.g. 2-(chloro, bromo or iodo)-ethyl, 3,3-difluoro- or dichloropropyl, 3,3,3-trichloropropyl, 3- or 4-chlorobutyl, 4,4- or 3,4-dichlorobutyl or 4,4,4-trifluorobutyl; unsubstituted or halogenated lower alkoxy- or alkylmercapto-lower alkyl, such as 2-ethoxyethyl, 3-methoxypropyl, 2-ethylmercapto-ethyl, 2-(2,2-dichloroethoxy)-ethyl, 2-(2-chloroethoxy)-ethyl, 2-(2,2,2-trifluoroethylmercapto)-ethyl or 2-(2,2-dichloroethylmercapto)-ethyl; carbamyl-lower alkyl or N,N-di-lower alkylcarbamyl-lower alkyl, such as carbamyl-methyl, N,N-dimethylcarbamyl-methyl, 2-carbamyl-ethyl or 2-N,N-diethyl-carbamyl-ethyl; sec. or tert. amino-lower alkyl, such as mono- or di-lower alkylamino-lower alkyl, lower alkyleneimino-lower alkyl, lower monoaza-, -oxa- or -thiaalkyleneimino-lower alkyl or N-lower alkyl-lower monoazaalkyleneimino-lower alkyl, e.g. 2-ethylamino-ethyl, 2-dimethylamino-ethyl, 3-diethylamino-propyl, 2-pyrrolidino-ethyl, 2-piperidino-ethyl 2-(4-methylpiperazino)-ethyl or 2-morpholino-ethyl; 5 to 7 ring-membered oxa-cycloalkyl or -cycloalkenyl, oxa-cycloalkyl- or -cycloalkenyl-lower alkyl, such as 3-tetrahydrofuryl, tetrahydrofuryl-2-methyl, (2-methyltetrahydrofuryl-2)-methyl, 2,3-dihydro- or tetrahydropyranyl-2-methyl.

An araliphatic radical $R_1$ preferably represents H-Ph-lower alkyl or -alkenyl or Hc-lower alkyl or -alkenyl in which the alkyl or alkenyl moiety preferably has up to 4 chain carbon atoms. Ph is a phenylene radical, e.g. such shown in Formula I, which is unsubstituted or substituted by one or more than one, preferably one or two substituents selected, for example, from lower alkyl, e.g. that mentioned above, free or functionally converted hydroxy or mercapto, such as lower alkoxy, lower alkylenedioxy, lower alkylmercapto or halogeno, e.g. methoxy, ethoxy, n- or i-propoxy or -butoxy, methylenedioxy, 1,1- or 1,2-ethylenedioxy, methyl- or ethylmercapto, fluoro, chloro or bromo; (hydroxy or halogeno)-lower alkyl or -alkoxy, e.g. 2-hydroxyethyl, trifluoromethyl or 2-hydroxyethoxy; nitro, amino, especially di-lower alkylamino, e.g. dimethylamino or diethylamino; or free or functionally converted carboxy or sulfo, e.g. lower carbalkoxy, carbamoyl, cyano or sulfamoyl; and Hc is a pyridyl, furyl or thienyl radical, which is unsubstituted or substituted by one or more than one, preferably one or two lower alkyl groups.

Preferred araliphatic or aromatic radicals $R_1$, $R_4$ and $R_5$—Ph are represented by the formulae H—Ph'—$C_mH_{2m}$, Hc'—$C_mH_{2m}$ and $H_2N$—Ph'—$C_mH_{2m}$ respectively, wherein Ph' is unsubstituted 1,2-phenylene, advantageously 1,3-phenylene or preferably 1,4-phenylene or such radicals substituted by one lower alkyl, hydroxy, lower alkoxy, halogeno or trifluromethyl, Hc' is unsubstituted 2-, 3-, or 4-pyridyl, 2- or 3-furyl or -thienyl or such radicals substituted by one or two lower alkyl groups and $m$ is an integer from 0 to 4.

Each of $R_2$, $R_3$ and $R_4$ is preferably hydrogen, but also lower alkyl, advantageously methyl. $R_4$, moreover represents preferably H—P' or $H_2N$—Ph', depending whether $R_5$ is amino or hydrogen respectively.

Preferred esters of the acids of Formula I are the methyl, ethyl, n- or i-propyl or -butyl esters and of the salts the ammonium, sodium, potassium, magnesium or calcium salts are preferred. Due to the amino groups present, also acid addition salts can be prepared, e.g. such of the therapeutically useful acids listed below.

The compounds of the invention exhibit valuable pharmacological properties. Primarily they show diuretic, natri- and chloriuretic activity with rapid onset of action, high urine but low potassium excretion levels. This can be demonstrated in animal tests using, for example mammals, e.g. rats or dogs, as test objects. Such tests can be performed, for example, by administering the compounds of the invention within a gelatin capsule to dogs, or in the form of aqueous solutions or starchy suspensions by stomach tube to rats, in an oral dosage range between about 0.01 and 50 mg/kg/day, preferably between about 0.1 and 10 mg/kg/day, advantageously between about 0.5 and 5 mg/kg/day. Simultaneously the test animals may receive various salt loads enterally or parenterally, for example, various amounts of subcutaneously applied 0.9% saline, e.g. 100 ml thereof per medium-sized dog (beagle). Urine is then collected, e.g. at 2 hour intervals, with or without catheterization, and its volume, sodium, potassium and chloride content estimated and compared with that of the same untreated or saline-treated animals. Besides the anti-edematous utility, the compounds of the invention can also be used as intermediates in the preparation of other valuable products, primarily of pharmacologically active compounds or compositions, e.g. such useful in the management of hypertension.

Preferred are those compounds of Formula I in which $R_1$ is lower alkyl, lower alkenyl, lower alkynyl, (monocyclic, 3 to 7 ring-membered cycloalkyl, cycloalkenyl, oxacycloalkyl, 2- or 7-norbornanyl or 2-norborn-5-enyl)-$C_mH_{2m}$; H—Ph'—$C_nH_{2n}$ or Hc'—$C_nH_{2n}$ wherein Ph' is 1,2-, 1,3- or 1,4-phenylene unsubstituted or substituted by one member of lower alkyl, hydroxy, lower alkoxy, halogeno or trifluoromethyl, Hc' is 2-, 3- or 4-pyridyl, 2- or 3-furyl or -thienyl unsubstituted or substituted by one or two lower alkyl groups, $m$ is an integer from 0 to 4 and $n$ is an integer from 1 to 4, each of $R_2$ and $R_3$ is hydrogen or lower alkyl, X is oxygen or sulfur, Ph is the above Ph', $R_4$ is hydrogen, lower alkyl or $R_6$—Ph' and one of $R_5$ and $R_6$ is amino and the other is hydrogen, or the lower alkyl esters, or therapeutically useful ammonium, alkali or alkaline earth metal or acid addition salts thereof.

Especially valuable are the compounds of Formula II

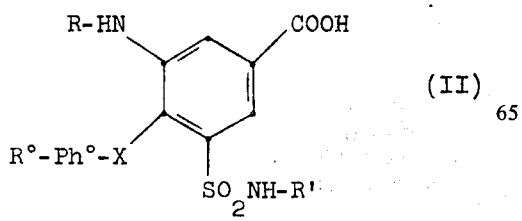

(II)

wherein R is alkyl or alkenyl with 3 to 7 carbon atoms, (3 to 7 ring-membered cycloalkyl, tetrahydrofuryl, 2- or 7-norbornanyl, 2-norborn-5-enyl, phenyl, tolyl, anisyl, halophenyl, furyl or thienyl)-methyl or -ethyl, X is oxygen or sulfur, Ph° is 1,2-, 1,3- or 1,4-phenylene, R' is hydrogen or Ph°—R'' and one of R° and R'' is amino and the other is hydrogen or therapeutically useful ammonium, alkali metal or acid addition salts thereof.

Outstanding are the compounds of Formula II, wherein R is alkyl or 2-alkenyl with 4 or 5 carbon atoms, cyclopropylmethyl, 2-tetrahydrofurylmethyl, 2-norborn-5-enylmethyl, benzyl or furfuryl, X is oxygen or preferably sulfur, Ph° is 1,4-phenylene, R° is amino and R' is hydrogen, or therapeutically useful ammonium, alkali metal or acid addition salts thereof.

Most preferred are the 4-(4-aminophenylmercapto)-3-(n-butyl, benzyl or furfuryl)-amino-5-sulfamoylbenzoic acids which, when given to rats or dogs at oral doses as low as 0.3 mg/kg/day, exhibit outstanding diuretic, natri- and chloriuretic effects.

The compounds of the invention are prepared according to methods in themselves known. Advantageously they are obtained by:

a. converting in a compound of Formula III

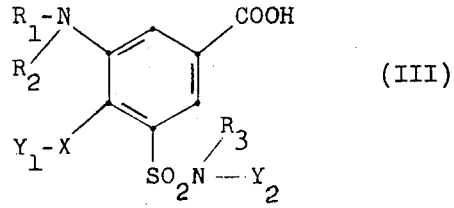

(III)

wherein one of $Y_1$ and $Y_2$ is an (acylamino, nitro or arylazo)-Ph radical and the other is $R_4$ or $R_5$-Ph respectively, or a lower alkyl ester or salt thereof, $Y_1$ or $Y_2$ into the corresponding aminophenyl group by hydrolysis or hydrogenation respectively or b. converting in a compound of Formula IV

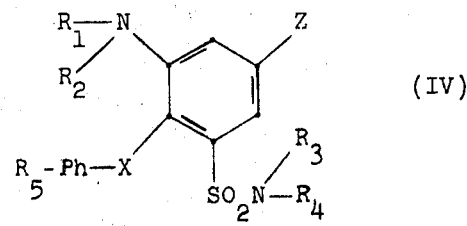

(IV)

wherein Z is a carbamoyl or aminocarbamoyl group, or a salt thereof, Z into carboxy, carbalkoxy or salified carboxy by hydrolysis or alcoholysis, or c. reacting a compound of Formula V

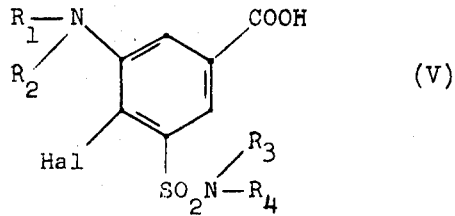

(V)

wherein Hal is a halogen atom, with a compound of the formula $R_5$—Ph—XH or an alkali metal salt thereof and, if desired, converting any resulting compound into another compound of the invention.

In said compounds of Formula III containing the (acylamino, nitro or arylazo)-Ph radical $Y_1$ or $Y_2$, the acylamino group is advantageously derived from either a lower alkanoic or carbonic acid lower alkyl ester and the arylazo group is preferably that of the formula H—Ph—N=N—. Said acylaminophenyl compounds, preferably the (lower alkanoyl- or lower alkoxy carbonylamino)-Ph, e.g. the (acetyl-, propionyl- or ethoxycarbonylamino)-Ph compounds, are converted into the compounds of the invention by hydrolysis, for example, with the use of aqueous bases, such as aqueous alkali metal hydroxides or carbonates or quaternary ammonium hydroxides, e.g. sodium hydroxide, potassium carbonate or trimethylbenzylammonium hydroxide. In case $Y_1$ or $Y_2$ stands for said (nitro or arylazo)-Ph group, it is converted into amino by conventional reduction, for example, with the use of catalytically activated or nascent hydrogen, e.g. hydrogen in the presence of platinum, palladium or nickel catalysts, e.g. Raney nickel, or generated by the action of non-precious metals, e.g. zinc or iron, on acids, such as mineral acids, e.g. hydrochloric or sulfuric acid, or with the use of reducing agents, preferably salts of elements of the 4th to 6th group of the Periodic Table and being in a low oxidation state, such as stannous or chromous halides, ammonium polysulfides or alkali metal hydrosulfites.

The carbamoyl or aminocarbamoyl group in said compounds of Formula IV is preferably unsubstituted but may also be substituted by lower alkyl, or aryl radicals, e.g. $R_1$, $R_5$—Ph or $Y_2$. The corresponding amides or hydrazides, e.g. the mono- or dimethylamide, diethylamide, i-propylamide; (benzyl, phenyl or acetylaminophenyl)-amide or the corresponding hydrazides are hydrolyzed or alcoholized to the compounds of Formula I, their lower alkyl esters or salts, according to conventional methods, advantageously with the use of aqueous or corresponding alcoholic bases, such as those described above, or lower alkanolic alkali metal alkoxides, e.g. ethanolic sodium ethoxide.

The phenols or thiophenols $R_5$—Ph—XH in process c) are preferably reacted in the form of their alkali metal salts, e.g. the sodium or potassium salts. The group Hal in the above compounds of Formula V is preferably fluorine, but also chlorine, bromine or iodine.

The compounds of the invention so obtained can be converted into each other according to known methods. For example, resulting compounds in which $R_2$ and/or $R_3$ stands for hydrogen, can be reacted with a reactive ester of a lower alkanol, for example, that of a hydrohalic or sulfonic acid, to yield the corresponding mono-, di- or tri-lower alkyl compounds. Resulting unsaturated compounds, e.g. lower alkenyl, alkynyl or furfuryl compounds, can be hydrogenated as shown above, to yield the corresponding saturated, e.g. lower alkyl or tetrahydrofurfuryl compounds. Resulting lower alkyl esters can also be hydrolyzed or transesterified, for example, with the use of the above alkaline hydrolyzing or alcoholizing agents.

The compounds of the invention are obtained in the free form or in the form of their salts, depending on the conditions under which the process is carried out, the salts are also included in the present invention. These are particularly derived from the free acids and therapeutically useful inorganic or organic bases, primarily the alkali metal, alkaline earth metal, e.g. sodium, potassium, magnesium or calcium salts, or ammonium salts derived from ammonia or amines, such as those corresponding to the amino group $R_1$—N—$R_2$, e.g. mono-, di- or tri-lower alkylamines, -cycloalkylamines, -cycloalkyl-lower alkylamines or -aralkylamines, mixed amines or tertiary nitrogen bases, such as pyridine, collidine or lutidine. Said compounds of Formula I also form acid addition salts, preferably with therapeutically useful acids, such as mineral acids, e.g. hydrochloric, hydrobromic, sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4-aminosalicylic, embonic, nicotinic, methanesulfonic, ethanesulfonic, hydroxy ethanesulfonic, ethylenesulfonic, halogen-benzenesulfonic, toluenesulfonic, naphthalenesulfonic or sulfanilic acid; methionine, tryptophane, lysine or arginine.

The invention further includes any variant of the present process in which an intermediate product obtainable at any stage of the process is used as starting material and any remaining steps are carried out, or the process is discontinued at any stage thereof, or in which the starting materials are formed under the reaction conditions, for example, amides of Formula IV from nitriles, or in which the reaction components are used in the form of their salts. Mainly those starting materials should be used in the reactions of the invention that lead to the formation of those compounds indicated above as being especially valuable.

The starting material is obtained according to known methods, preferably those illustrated by the examples herein. For example, the compounds of Formula III are obtained by condensing reactive esters of the alcohols $R_1$—OH, e.g. those mentioned above, or corresponding aldehydes with compounds of the Formula VI

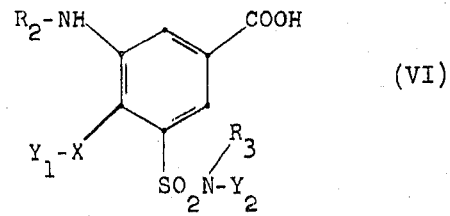

(VI)

(obtainable according to the methods disclosed in J. Med. Chem., 1971, Vol. 14, No. 5, page 432) and hydrogenating any Schiff's base obtained, e.g. as shown above, or with the use of complex light metal hydrides, such as alkali metal borohydrides, e.g. sodium borohydride. Compounds of Formulae III and IV can also be prepared by reacting corresponding phenols or thiophenols of the formulae $Y_1$—X—H or $R_5$—Ph—X—H, preferably their alkali metal salts, e.g. sodium or potassium salts, with compounds of the Formula VII

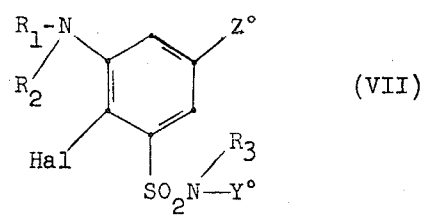

(VII)

wherein Z° is a free or correspondingly esterified or amidated carboxy group and Y° is either $Y_2$ or $R_4$, and the other symbols have the meaning given above, preferably at elevated temperature and/or pressure. Representative members of said halogenated acids, or lower alkyl esters thereof, are described in J. Med. Chem., 1970, Vol. 13, No. 6, page 1071, showing also various methods according to which the above intermediates can be prepared. The corresponding amides or hydrazides are obtainable from said esters by ammono- or hydrazinolysis, which process may take place simultaneously in the above condensation, when using compounds in which Z° is lower carbalkoxy.

Resulting mixtures of isomers, e.g. of compounds of Formulae I to VII, can be separated into the single isomers by methods in themselves known, e.g. by fractional distillation, crystallization and/or chromatography. Racemic products can likewise be resolved into the optical antipodes, for example by separation of diastereomeric salts thereof, e.g. by the fractional crystallization of d- or l-tartrates or d-$\alpha$-(phenyl or 1-naphthyl)-ethylamine or 1-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or advantageously elevated temperatures, at atmospheric or superatmospheric pressure.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances, e.g. antihypertensives and/or psychotherapeutics, as illustrated by U.S. Pat. Nos. 3,288,678, 3,379,612, 3,499,082 and 3,515,786. Said pharmaceutical compositions are prepared according to conventional mixing, granulating or coating methods respectively and contain about 0.1 to 75%, preferably about 1 to 50% of the active ingredient.

The following examples illustrating the invention are not to be construed as being limitations thereon. Temperatures are given in degrees Centigrade and all parts wherever given are parts by weight.

EXAMPLE 1

The mixture of 1.9 g of 4-(4-acetamidophenoxy)-3-n-butylamino-5-sulfamoylbenzoic acid and 19 ml of 2N aqueous sodium hydroxide is refluxed for one hour under nitrogen. After cooling to room temperature it is filtered, the filtrate acidified with glacial acetic acid to a pH of 4-5, the precipitate formed filtered off, washed with water and recrystallized from 50% aqueous ethanol, to yield the 4-(4-aminophenoxy)-3-n-butylamino-5-sulfamoylbenzoic acid of the formula

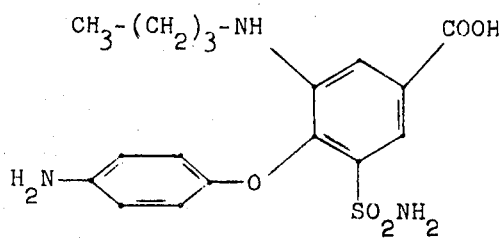

melting at 264° with decomposition.

The starting material is prepared as follows: The mixture of 14 g of 4-chloro-3-nitro-5-sulfamoylbenzoic acid, 200 ml of 1N aqueous sodium bicarbonate and 15.9 g of 4-acetamidophenol is heated to about 95°–100°C for 21 hours while stirring under nitrogen. It is cooled to room temperature and made strongly acidic with concentrated hydrochloric acid. The precipitate formed is filtered off, to yield the 4-(4-acetamidophenoxy)-3-nitro-5-sulfamoylbenzoic acid, which after trituration with aqueous ethanol melts at 293° with decomposition.

The mixture of 9.5 g thereof, 100 ml of water, 1 g of sodium hydroxide and 2.5 g of 10% palladium on charcoal is hydrogenated at room temperature and 2.8 atm until the theoretical amount of hydrogen has been absorbed. It is filtered, the filtrate acidified with concentrated hydrochloric acid, the precipitate formed filtered off, washed with water and triturated with aqueous ethanol, to yield the 4-(4-acetamidophenoxy)-3-amino-5-sulfamoylbenzoic acid melting at 305° with decomposition.

5.5 g thereof are dissolved in 10 ml of N aqueous sodium hydroxide and 30 ml of water, the pH of the solution kept at 7.4 by the dropwise addition of 4N aqueous sodium hydroxide while 2 g of 1-bromo-2-butene are added at room temperature and the mixture stirred for about 17 hours. The mixture is filtered, the filtrate acidified to pH = 4 with glacial acetic acid and the precipitate formed filtered off. It is taken up in 10 ml of 50% hot aqueous ethanol, the mixture diluted with 25 ml of ethanol-water (1:2) and the precipitate formed in the cold filtered off, to yield the 4-(4-acetamidophenoxy)-3-(2-butenylamino)-5-sulfamoylbenzoic acid, melting at 255°–257° with decomposition.

The solution of 1.9 g thereof in 150 ml of anhydrous ethanol is hydrogenated over 0.2 g of platinum oxide at room temperature and atmospheric pressure. After the theoretical amount of hydrogen has been absorbed, the mixture is filtered and the filtrate evaporated, to yield the 4-(4-acetamidophenoxy)-3-n-butylamino-5-sulfamoylbenzoic acid.

EXAMPLE 2

The mixture of 0.9 g of 4-(4-acetamidophenoxy)-3-(2-butenylamino)-5-sulfamoylbenzoic acid and 9 ml of 2N aqueous sodium hydroxide is refluxed for one hour under nitrogen. After cooling to room temperature it is filtered, the filtrate acidified with glacial acetic acid to pH = 4 and the supernatant solution decanted off. It is further acidified with concentrated hydrochloric acid to pH = 1 and the precipitate formed after cooling filtered off and washed with cold water, to yield the 4-(4-aminophenoxy)-3-(2-butenylamino)-5-sulfamoylbenzoic acid hydrochloride or the formula

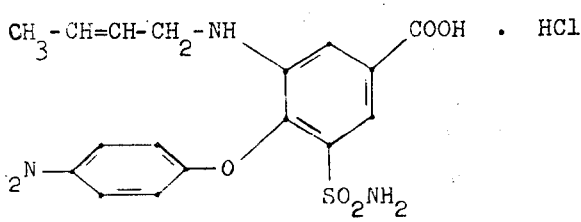

melting at 271° with decomposition.

EXAMPLE 3

The mixture of 2.8 g of 4-(4-acetamidophenylmercapto)-3-n-butylamino-5-sulfamoylbenzoic acid and 28 ml of 2N aqueous sodium hydroxide is refluxed for one hour under nitrogen. After cooling to room temperature it is filtered, the filtrate acidified with glacial acetic acid to a pH of 4–5, the precipitate formed filtered off, washed with water and recrystallized from 50% aqueous ethanol, to yield the 4-(4-aminophenylmercapto)-3-n-butylamino-5-sulfamoylbenzoic acid of the formula

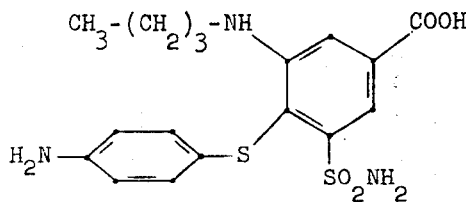

melting at 236° with decomposition.

The starting material is prepared as follows: The mixture of 19.6 g of 4-chloro-3-nitro-5-sulfamoylbenzoic acid, 280 ml of N aqueous sodium hydroxide and 11.8 g of 4-acetamidothiophenol is stirred for 24 hours at room temperature under nitrogen. It is filtered, the filtrate made strongly acidic with concentrated hydrochloric acid, the precipitate formed filtered off and recrystallized from 50% aqueous ethanol, to yield the 4-(4-acetamidophenylmercapto)-3-5-sulfamoylbenzoic acid, melting at 168°.

8.2 g thereof are added portionwise to the mixture of 16 g of iron powder, 1.7 g of ammonium chloride, 70 ml of water and 0.8 ml of N hydrochloric acid while stirring. After heating it for four hours at the steam bath it is filtered hot, the precipitate taken up in 200 ml of N aqueous sodium hydroxide and the solution filtered. The filtrates are acidified with concentrated hydrochloric acid and the precipitate formed recrystallized from 50% aqueous ethanol, to yield the 4-(4-acetamidophenylmercapto)-3-amino-5-sulfamoylbenzoic acid melting at 207°.

3.8 g thereof are dissolved in 50 ml of water containing 0.4 g of sodium hydroxide, the pH of the solution kept at 7.4 by the dropwise addition of 4N aqueous sodium hydroxide and 1.4 g of 1-bromo-2-butene are added at room temperature. The mixture is stirred for about one hour, filtered, the filtrate acidified to a pH of 4–5 with glacial acetic acid and the precipitate formed filtered off. It is recrystallized from aqueous ethanol, to yield the 4-(4-acetamidophenylmercapto)-3-(2-butenylamino)-5-sulfamoylbenzoic acid, melting at 148°.

The solution of 2.75 g thereof in 750 ml of anhydrous ethanol is hydrogenated over 0.2 g of platinum oxide at room temperature and atmospheric pressure. After the theoretical amount of hydrogen has been absorbed, the mixture is filtered hot and the filtrate evaporated, to yield the 4-(4-acetamidophenylmercapto)-3-n-butylamino-5-sulfamoylbenzoic acid.

EXAMPLE 4

The mixture of 1.2 g of 4-(4-acetamidophenylmercapto)-3-(2-butenylamino)-5-sulfamoylbenzoic acid and 12 ml of 2N aqueous sodium hydroxide is refluxed for one hour under nitrogen. After cooling to room temperature it is filtered, the filtrate acidified with glacial acetic acid to a pH of 4–5 and the precipitate formed filtered off. It is washed with water and recrystallized from 50% aqueous ethanol, to yield the 4-(4-aminophenylmercapto)-3-(2-butenylamino)-5-sulfamoylbenzoic acid, melting at 242°.

EXAMPLE 5

The mixture of 1.4 g of 4-(4-acetamidophenoxy)-3-benzylamino-5-sulfamoylbenzoic acid and 14 ml of 2N aqueous sodium hydroxide is refluxed for one hour under nitrogen. After cooling to room temperature it is filtered and the filtrate acidified with glacial acetic acid to pH = 4. The precipitate formed is filtered off and recrystallized from aqueous ethanol, to yield the 4-(4-aminophenoxy)-3-benzylamino-5-sulfamoylbenzoic acid of the formula

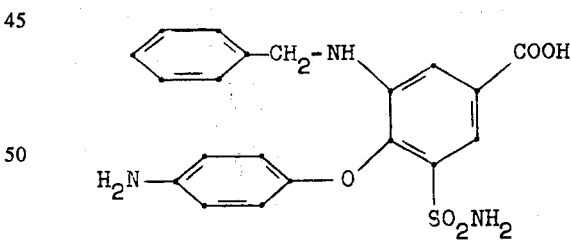

melting at 272° with decomposition.

The starting material is prepared as follows: To the mixture of 3.6 g of 4-(4-acetamidophenoxy)-3-amino-5-sulfamoylbenzoic acid, 10 ml of water and the sufficient amount of N aqueous sodium hydroxide to reach a pH = 7.4, 1.3 g of benzyl chloride are added while stirring at 30°. The mixture is stirred for 16 hours at room temperature, during which time 4N aqueous sodium hydroxide is added dropwise to keep said pH value. It is filtered, the filtrate acidified with glacial acetic acid and the precipitate formed filtered off, to yield the 4-(4-acetamidophenoxy)-3-benzylamino-5-sulfamoylbenzoic acid which, on recrystallization from aqueous ethanol, melts at 255° with decomposition.

EXAMPLE 6

The mixture of 2.5 g of 4-(4-acetamido-3-tolyloxy)-3-benzylamino-5-sulfamoylbenzoic acid and 25 ml of 2N aqueous sodium hydroxide is refluxed for seven hours under nitrogen. After cooling it is filtered, the filtrate acidified to a pH of 4–5 with glacial acetic acid, the precipitate formed filtered off, washed with water and recrystallized from 50% aqueous ethanol, to yield the 4-(4-amino-3-tolyloxy)-3-benzylamino-5-sulfamoylbenzoic acid of the formula

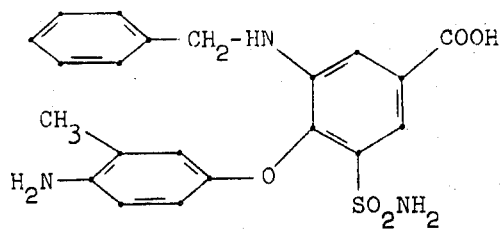

melting at 266°.

The starting material is prepared as follows: The mixture of 14 g of 4-chloro-3-nitro-5-sulfamoylbenzoic acid, 200 ml of water, 16.8 g of sodium bicarbonate and 17.3 g of 4-acetamido-m-cresol is stirred for 14 hours at 90°–95° under nitrogen. After cooling it is acidified with concentrated hydrochloric acid, the supernatant solution decanted off and the residue taken up in 70 ml of hot ethanol, followed by 70 ml of water and the precipitate formed in the cold filtered off, to yield the 4-(4-acetamido-3-tolyloxy)-3-nitro-5-sulfamoylbenzoic acid melting at 238°–240°.

The mixture of 6.3 g thereof, 70 ml of water and 8 ml of 2N aqueous sodium hydroxide is hydrogenated over 1 g of 10% palladium on charcoal until the theoretical amount of hydrogen has been absorbed. It is filtered, the filtrate acidified with hydrochloric acid, the precipitate formed filtered off and recrystallized from 75% aqueous ethanol, to yield the 4-(4-acetamido-3-tolyloxy-3-amino-5-sulfamoylbenzoic acid melting above 280°.

The solution of 3.7 g thereof in 10 ml of water and 5 ml of N aqueous sodium hydroxide is adjusted to pH = 7.4 by the addition of 4N aqueous sodium hydroxide after which 1.3 g of benzylchloride are added while stirring at room temperature under nitrogen. During the following 41 hours water is added to facilitate stirring. The mixture is filtered, the filtrate acidified with glacial acetic acid to a pH 4–5 and the precipitate formed recrystallized from 50% aqueous ethanol, to yield the 4-(4-acetamido-3-tolyloxy)-3-benzylamino-5-sulfamoylbenzoic acid melting at 203°.

EXAMPLE 7

The mixture of 2.2 g of 4-(4-acetamidophenylmercapto)-3-benzylamino-5-sulfamoylbenzoic acid and 22 ml of 2N aqueous sodium hydroxide is refluxed for one hour under nitrogen. After cooling it is filtered, the filtrate acidified with glacial acetic acid to pH = 4. The precipitate formed is filtered off and recrystallized from 50% aqueous ethanol, to yield the 4-(4-aminophenylmercapto)-3-benzylamino-5-sulfamoylbenzoic acid melting at 254°–256°.

The starting material is prepared as follows: The solution of 4-(4-acetamidophenylmercapto)-3-amino-5-sulfamoylbenzoic acid in 50 ml of water containing 0.4 g of sodium hydroxide is adjusted to pH = 7.4 by the addition of 4N aqueous sodium hydroxide, whereupon 1.3 g of benzylchloride are added while stirring under nitrogen. As soon as the pH remains constant the mixture is filtered and the filtrate acidified with glacial acetic acid to a pH of 4–5. The precipitate formed is recrystallized from 50% aqueous ethanol, to yield the 4-(4-acetamidophenylmercapto)-3-benzylamino-5-sulfamoylbenzoic acid melting at 255°–258°.

EXAMPLE 8

The mixture of 1.1 g of 4-(4-acetamidophenoxy)-3-furfurylamino-5-acetylsulfamoylbenzoic acid and 11 ml of 2N aqueous sodium hydroxide is refluxed for two hours under nitrogen. After cooling to room temperature it is filtered, the filtrate acidified with glacial acetic acid to a pH of 4–5 and the precipitate formed filtered off. It is recrystallized from 70% aqueous ethanol, to yield the 4-(4-aminophenoxy)-3-furfurylamino-5-sulfamoylbenzoic acid melting at 233°–235°.

The starting material is prepared as follows: The mixture of 12.5 g of 4-(4-acetamidophenoxy)-3-nitro-5-sulfamoylbenzoic acid and 125 ml of acetic anhydride is refluxed for two hours under nitrogen and evaporated under reduced pressure. The residue is taken up in 125 ml of 2N aqueous sodium hydroxide and 25 ml of water, the solution washed with diethyl ether, filtered and the filtrate acidified with concentrated hydrochloric acid and the precipitate recrystallized from 33 and 50% aqueous ethanol, to yield the 4-(4-acetamidophenoxy)-3-nitro-5-acetylsulfamoylbenzoic acid decomposing at about 240°. The solution of 10.5 g thereof in 100 ml of water and 22 ml of 2N aqueous sodium hydroxide is hydrogenated over 2.5 g of 10% palladium on charcoal until the theoretical amount of hydrogen has been absorbed. The mixture is filtered, the filtrate acidified with concentrated hydrochloric acid and the precipitate recrystallized from aqueous ethanol, to yield the 4-(4-acetamidophenoxy)-3-amino-5-acetylsulfamoylbenzoic acid melting at 305°–306° with decomposition.

The mixture of 2.4 g thereof and 24 ml of furfural is heated to 90°–95° for 18 hours while stirring under nitrogen. It is filtered hot and the filtrate evaporated under reduced pressure, to yield the corresponding Schiff's base. To the solution of 1.5 g thereof in 80 ml of ethanol, 3.3 g of sodium borohydride are added portionwise during 20 minutes while stirring and cooling with ice. Thereupon the mixture is stirred for 18 hours under nitrogen, 1.8 g of additional sodium borohydride are added and the mixture stirred 90 minutes longer. Thereupon 130 ml of water are added, the mixture concentrated under reduced pressure, the concentrate acidified with concentrated hydrochloric acid and the precipitate recrystallized from 50% aqueous ethanol, to yield the 4-(4-acetamidophenoxy)-3-furfurylamino-5-acetylsulfamoylbenzoic acid melting at 250° with decomposition.

EXAMPLE 9

The mixture of 2.3 g of 4-(4-acetamidophenylmercapto)-3-furfurylamino-5-sulfamoylbenzoic acid and 23 ml of 2N aqueous sodium hydroxide is refluxed for one hour under nitrogen. After cooling to room temperature it is acidified to pH = 5 and the precipitate formed filtered off. It is dissolved in 25 ml of 50% hot aqueous ethanol, the solution cooled to room temperature and decanted from some amorphous substance.

The supernatant solution is allowed to stand at room temperature for a longer period of time, the precipitate formed filtered off and this recrystallization procedure repeated several times, to yield the 4-(4-aminophenylmercapto)-3-furfurylamino-5-sulfamoylbenzoic acid, starting to melt at about 125°.

The starting material is prepared as follows: The mixture of 2 g of 4-(4-acetamidophenylmercapto)-3-amino-5-sulfamoylbenzoic acid, 1 g of furfural and 20 ml of diethyleneglycol dimethyl ether is heated to 105° for 22 hours while stirring under nitrogen. It is evaporated under reduced pressure, the residue taken up in 75 ml of ethanol and 1 g of sodium borohydride is added portionwise while stirring at room temperature under nitrogen. After stirring overnight, 75 ml of water are added and the mixture filtered. The filtrate is concentrated under reduced pressure, the concentrate acidified with concentrated hydrochloric acid and the precipitate formed filtered off, to yield the 4-(4-acetamidophenylmercapto)-3-furfurylamino-5-sulfamoylbenzoic acid.

EXAMPLE 10

The mixture of 2.5 g of 4-phenoxy-3-benzylamino-5-(2-acetamidophenylsulfamoyl)-benzoic acid and 25 ml of 2N aqueous sodium hydroxide is refluxed for four hours under nitrogen. After cooling to room temperature it is filtered, the filtrate acidified with glacial acetic acid to pH = 2 and the precipitate recrystallized from ethanol, to yield the 4-phenoxy-3-benzylamino-5-(2-aminophenylsulfamoyl)-benzoic acid of the formula

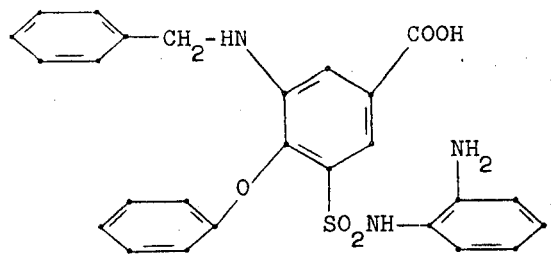

melting at 113°–116°.

The starting material is prepared as follows: The mixture of 38.8 g 4-chloro-5-chlorosulfonyl-3-nitrobenzoic acid, 39.9 g of 2-aminoacetanilide and 150 ml of dimethylformamide is stirred for 2 ½ hours at room temperature. It is poured into 1.7 l t of water and 20 ml of concentrated hydrochloric acid while stirring, the precipitate formed is filtered off and washed with water. It is dissolved in 600 ml of hot ethanol, 900 ml of hot water are added, the mixture filtered and the filtrate left in the cold, to yield the 4-chloro-5-(2-acetamidophenylsulfamoyl)-3-nitrobenzoic acid melting at 225°–227° with decomposition.

The mixture of 6.3 g thereof, 3 g of phenol, 5.4 g of sodium bicarbonate and 45 ml of water is heated to 140° for 16 hours. After cooling it is diluted with 50 ml of water, acidified with hydrochloric acid to pH = 2, the liquid phase decanted off and the residue triturated with water, diethyl ether and ethanol, to yield the 4-phenoxy-5-(2-acetamidophenylsulfamoyl)-3-nitrobenzoic acid melting at 240°–244° with decomposition.

The solution of 4.7 g thereof in 100 ml of water and 9 ml of 2N aqueous sodium hydroxide is hydrogenated over 1.2 g of 10% palladium on charcoal at room temperature at 2.8 atm until the theoretical amount of hydrogen has been absorbed. The mixture is filtered, the filtrate acidified with hydrochloric acid to pH = 2, the precipitate filtered off and dissolved in 60 ml of hot ethanol. The solution is diluted with 60 ml of water and the precipitate formed collected to yield the 4-phenoxy-3-amino-5-(2-acetamidophenylsulfamoyl)-benzoic acid melting at 224°–226°.

The mixture of 3.1 g thereof and 25 ml of benzaldehyde is heated to 110° for four hours and evaporated under reduced pressure at about 100° for one hour. The residue is taken up in 75 ml of ethanol, 3.5 g of sodium borohydride are added while stirring and keeping the temperature at 20°–30°. After stirring overnight at room temperature another 1.3 g of sodium borohydride are added, stirring is continued for 90 minutes and 50 ml of water are added. The mixture is filtered, the filtrate acidified with hydrochloric acid to pH = 2, the precipitate formed filtered off and recrystallized from 50% aqueous ethanol, to yield the 4-phenoxy-3-benzylamino-5-(2-acetamidophenylsulfamoyl)-benzoic acid melting at 197°–200°.

EXAMPLE 11

The mixture of 3 g of 4-phenoxy-3-furfurylamino-5-(2-acetamidophenylsulfamoyl)-benzoic acid and 30 ml of 2N aqueous sodium hydroxide is refluxed for 4 ½ hours. After cooling to room temperature it is acidified with hydrochloric acid to pH = 2. The precipitate formed is filtered off and recrystallized from aqueous ethanol, to yield the 4-phenoxy-3-furfurylamino-5-(2-aminophenylsulfamoyl)-benzoic acid melting at 105°–110° with decomposition.

The starting material is prepared as follows: The mixture of 3.5 g of 4-phenoxy-3-amino-5-(2-acetamidophenylsulfamoyl)-benzoic acid and 30 ml of furfural is heated to 100° for five hours and allowed to stand at room temperature for 16 hours. It is evaporated under reduced pressure, the residue triturated with diethyl ether and dissolved in 75 ml of ethanol. Thereupon 2 g of sodium borohydride are added while stirring and cooling followed by another 0.5 g thereof after 4 hours and another 0.5 g thereof after 16 hours and stirring is continued for one hour. Thereupon 100 ml of water are added, the mixture filtered and the filtrate acidified with hydrochloric acid to a pH of 2–3. The precipitate formed is filtered off and recrystallized from 30% aqueous ethanol to yield the 4-phenoxy-3-furfurylamino-5-(2-acetamidophenylsulfamoyl)-benzoic acid melting at 207°–210° with decomposition.

EXAMPLE 12

Preparation of 10,000 tablets each containing 5 mg of the active ingredient:

Formula:

| | |
|---|---|
| 4-(4-aminophenylmercapto)-3-n-butylamino-5-sulfamoylbenzoic acid | 50.0 g |
| Lactose | 1,207.0 g |
| Corn starch | 75.0 g |
| Polyethylene glycol 6.000 | 75.0 g |
| Talcum powder | 75.0 g |
| Magnesium stearate | 18.0 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

Similarly, 5 mg tablets are prepared from the remaining compounds of the invention, e.g. those illustrated by the previous examples.

I claim:
1. A pharmaceutical composition comprising a diuretically effective amount of a compound corresponding to the formula

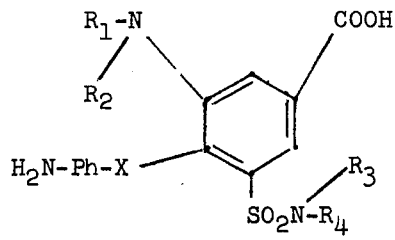

in which $R_1$ is lower alkyl, lower alkenyl, cycloalkyl or cycloalkyl-lower alkyl, each of which with 3 to 7 ring carbon atoms, Ph is unsubstituted phenylene or phenylene substituted by one member of lower alkyl, each of $R_2$, $R_3$ and $R_4$ is hydrogen or lower alkyl, and X is oxygen or sulfur, or the lower alkyl esters or therapeutical useful ammonium, alkali or alkaline earth metal or acid addition salts thereof, together with a pharmaceutical excipient.

2. A composition as claimed in claim 1, wherein the active compound is that corresponding to the formula

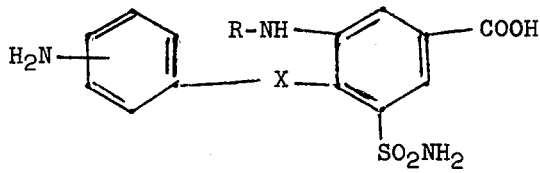

wherein R is alkyl or 2-alkenyl with 4 to 5 carbon atoms, or cyclopropylmethyl and X is oxygen or sulfur, or therapeutically useful ammonium, alkali metal or acid addition salts thereof.

3. A composition as claimed in claim 1, wherein the active compound is the 4-(4-aminophenylmercapto)-3-n-butylamino-5-sulfamoylbenzoic acid.

4. A method of treating edema in mammals, which comprises administering to them enterally or parenterally a diuretically effective amount of a compound of claim 1.

* * * * *